(12) United States Patent
Mayoral

(10) Patent No.: US 7,318,830 B2
(45) Date of Patent: Jan. 15, 2008

(54) APPARATUS AND METHOD OF USE OF A CIRCULAR SURGICAL STAPLER

(76) Inventor: Jaime L. Mayoral, 504 Tomahawk, San Antonio, TX (US) 78205

( * ) Notice: Subject to any disclaimer, the term of this patent is extended or adjusted under 35 U.S.C. 154(b) by 801 days.

(21) Appl. No.: 10/822,346

(22) Filed: Apr. 12, 2004

(65) Prior Publication Data

US 2005/0228414 A1 Oct. 13, 2005

(51) Int. Cl.
*A61B 17/04* (2006.01)
(52) U.S. Cl. .................................... 606/139; 606/159
(58) Field of Classification Search ............... 606/111, 606/112, 114, 115, 139, 142, 144, 151, 157, 606/159, 219
See application file for complete search history.

(56) References Cited

U.S. PATENT DOCUMENTS 6,716,222 B2 * 4/2004 McAlister et al. .......... 606/139
7,128,748 B2 * 10/2006 Mooradian et al. ......... 606/151

\* cited by examiner

*Primary Examiner*—Kevin T. Truong

(57) ABSTRACT

A method and apparatus for removing a circumferential portion of a hollow body organ from a patient with a circular stapling instrument. The instrument is provided with a vacuum tubing in communication with an inner chamber within the head assembly of the stapler. A negative pressure is drawn through the tubes and hemorrhoidal tissue is drawn into the inner chamber. An anvil member is closed around the hemorrhoidal tissue thereby pinching the drawn tissue between the anvil and the head assembly housing. The stapler is fired and the hemorrhoid is transected and retained within the inner chamber. The evacuation is shut off and the stapler is removed with the transected tissue.

1 Claim, 5 Drawing Sheets

APPARATUS AND METHOD OF USE OF A CIRCULAR SURGICAL STAPLER

BACKGROUND OF THE INVENTION

This invention relates to an improved surgical stapling instrument and method for joining hollow body organs, including but not limited to the bowels, rectum and intestines. More particularly, the present invention relates to the use of an evacuating stapling head assembly in cooperation with an anvil assembly to draw a portion of the hollow body organ into the head for transecting the drawn portion and stapling the ends of the remaining organ section to close the transaction site.

Circular surgical stapling devices are well known in the art. U.S. Pat. Nos. 5,522,543 and 6,083,241 are typical of this prior art. Particularly informative of the state of the art is U.S. Pat. No. 6,102,271 to Lango, et al., which patent disclosure is incorporated herein for all purposes.

Stapled rectal mucosectomy or anopexy consist in the relocation of prolapsing hemorrhoids to their anatomical place within the anal canal by means of a circumferential resection of the redundant mucosa situated above the hemorrhoids.

The most difficult step in the procedure for mucosa prolapse and hemorrhoids is placement of the purse-string suture. U.S. Pat. No. 6,102,271 discloses the step of the procedure in sufficient detail for comprehension by one of ordinary skill in the art. Briefly, the purse string is placed using the purse string anoscope in a circumferential manner at 4 cm proximal to the dentate line. Placing the purse string at the correct position can be difficult due to poor lighting and visualization of the anal canal through the purse string device. There has been an association between incorporating longitudinal muscle fibers of the rectum and fibers of the internal anal sphincter in the resected doughnut. The development of severe anal pain, fecal urgency and even some cases of perforation with local sepsis can be associated to purse string misplacement. It is believed that the technical issues regarding these complications have to do with the misplacement of the purse-string suture. The present invention method and apparatus completely eliminates the need for this risky purse-string suturing step in a hemorrhoidectomy.

SUMMARY OF THE INVENTION

The present invention includes a circular stapler having a sealed housing or casing and a mechanism for developing a negative pressure or suction within the housing. Suction is applied to draw the prolapsed mucous membrane into the stapling device. An appropriate level of section is dependent upon the structural strength of the patient's membrane. Normal evacuating pressures are in the range of about 80 psi to about 300 psi. Only sufficient suction pressure to incorporate the mucous membrane is applied leaving out the rectal wall.

The present invention method involves the introduction of a circular anal cannula. This reduces the prolapse and parts of the anal mucous membrane. The cannula is then fixed to the anal verge with four stitches at the flange edges of the cannula.

The casing of the inventive circular stapler is then introduced to approximately 2 cm proximal to the dentate line and is opened to its maximum position. Then an effective amount of suction is applied so that there is a complete draw of all the mucous prolapse and hemorrhoid tissue into the casing of the circular stapler. The stapler is then closed or tightened and fired. It is closed for 20 seconds after firing to help promote hemostasis. The instrument is slightly open for extraction. The staple line is checked for bleeding and additional sutures may be placed, as necessary.

DETAILED DESCRIPTION OF THE PREFERRED EMBODIMENTS

U.S. Pat. No. 6,102,271 (incorporated herein) provides an excellent disclosure of the basic construction of a prior art stapler prior to being modified into the present invention. A complete description of the underlying instrument maybe fully understood therein, except for the incorporation of a suction mechanism to draw the hemorrhoid or other hollow body organ into the inner chamber of the modified stapler.

Figure 1:
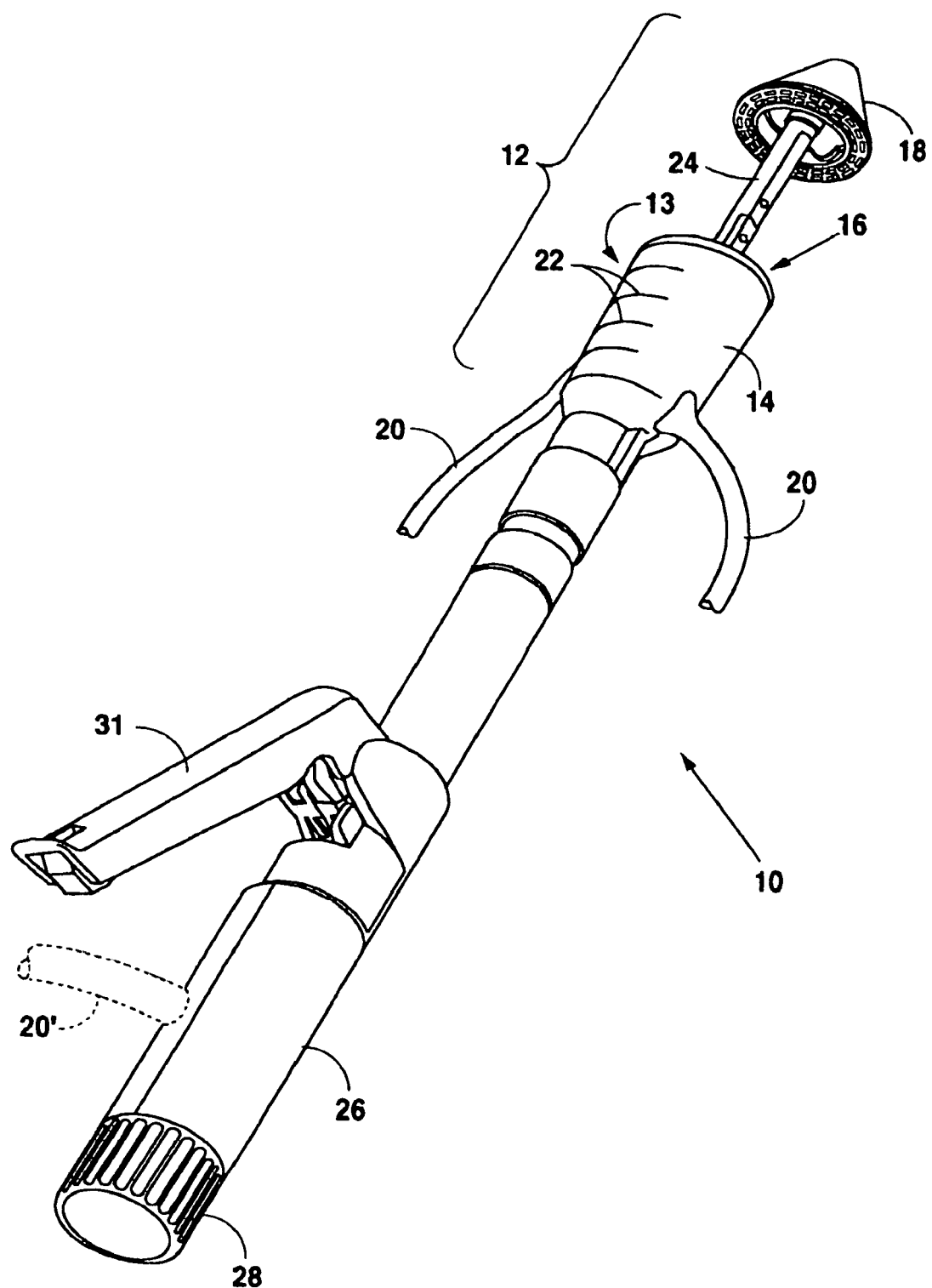
FIG. 1 illustrates a prospective view of the stapler of the present invention in the open position.

FIG. 1 illustrates a circular stapling instrument 10 having a head assembly 12, an outer housing 14 with an inner chamber 16 and an anvil assembly 18. The outer housing 14 is adapted to receive and retain a first end vacuum tubing 20 with the section of the tubing attached to a vacuum pump (not shown) to draw a negative pressure inside the housing 14 and within the inner chamber 16. One of ordinary skill in the art will know how to attach the tubing to such a vacuum pump to achieve a controllable negative pressure.

Figure 3:
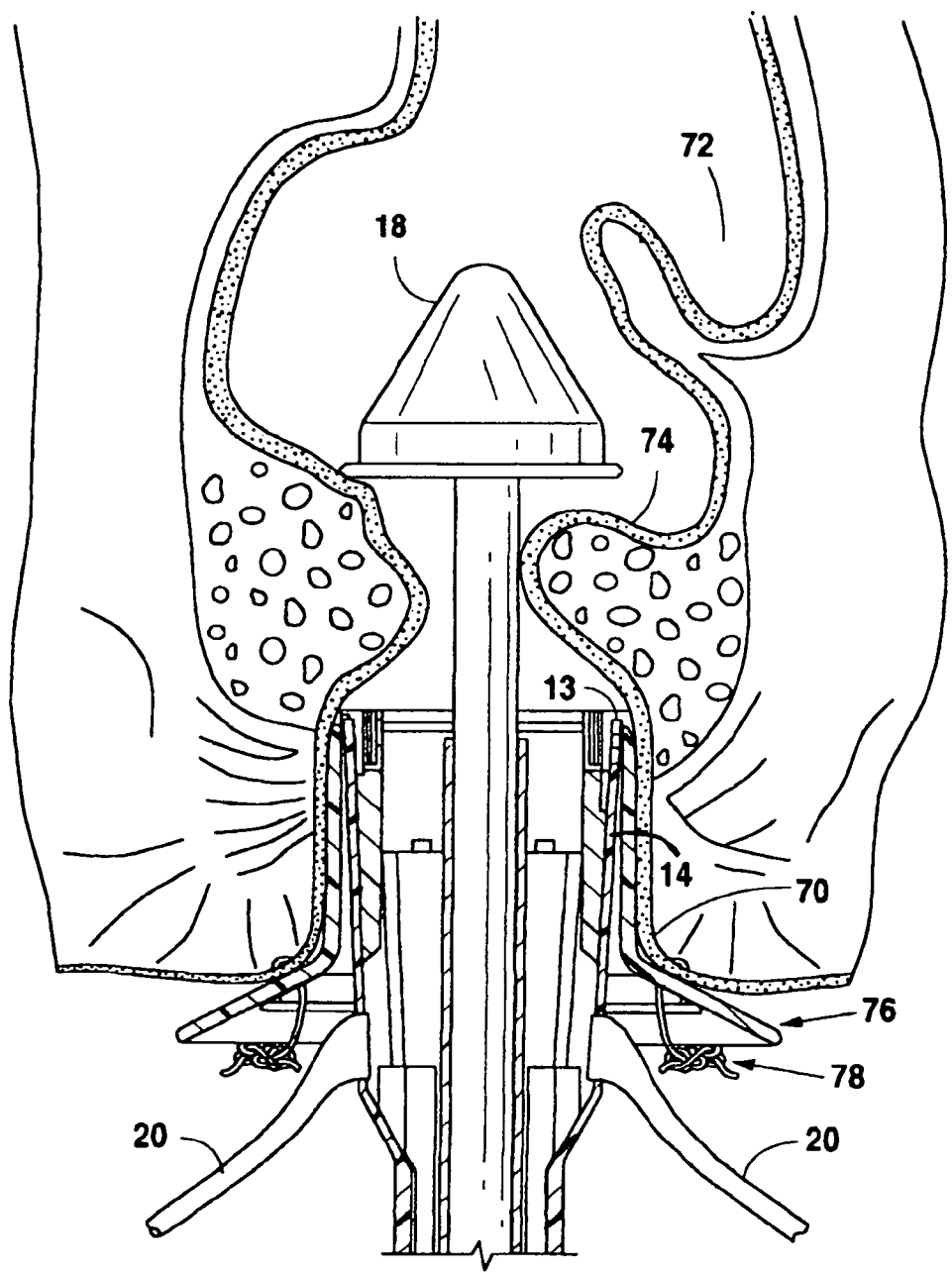
FIG. 3 is a cross-sectional view of an anal introducer inserted into the anus of a patient wherein the anal cannula of the introducer is sutured into position and the surgical stapler in the open position has been inserted into the anus and suction initiated.
Figure 4:
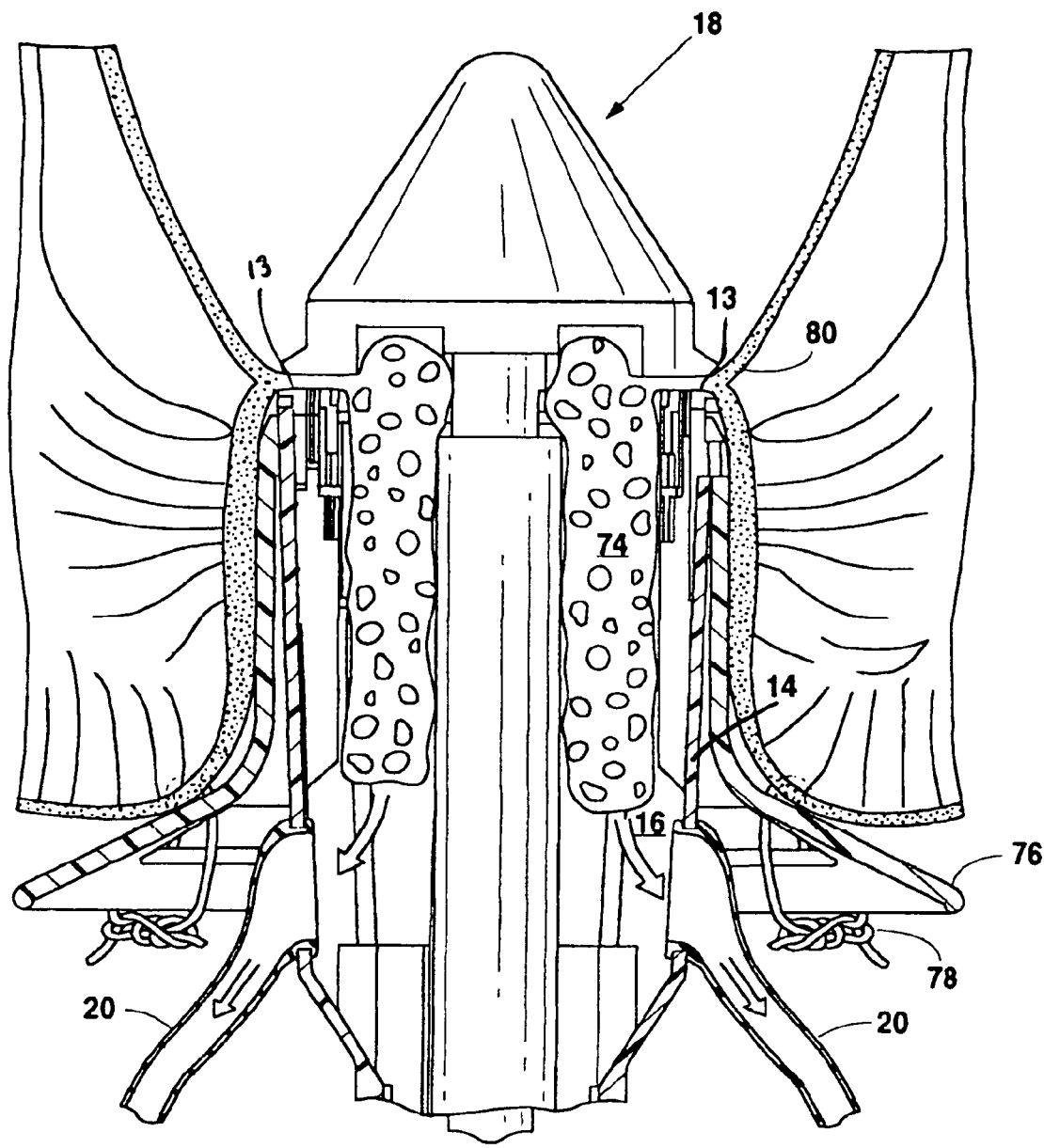
FIG. 4 is a cross-sectional view similar to FIG. 3, but the hemorrhoids have been drawn into the inner chamber of the stapler by the suction mechanism and the anvil assembly of the stapler head end has been closed upon the hemorrhoids prior to firing the stapler.
Figure 5:
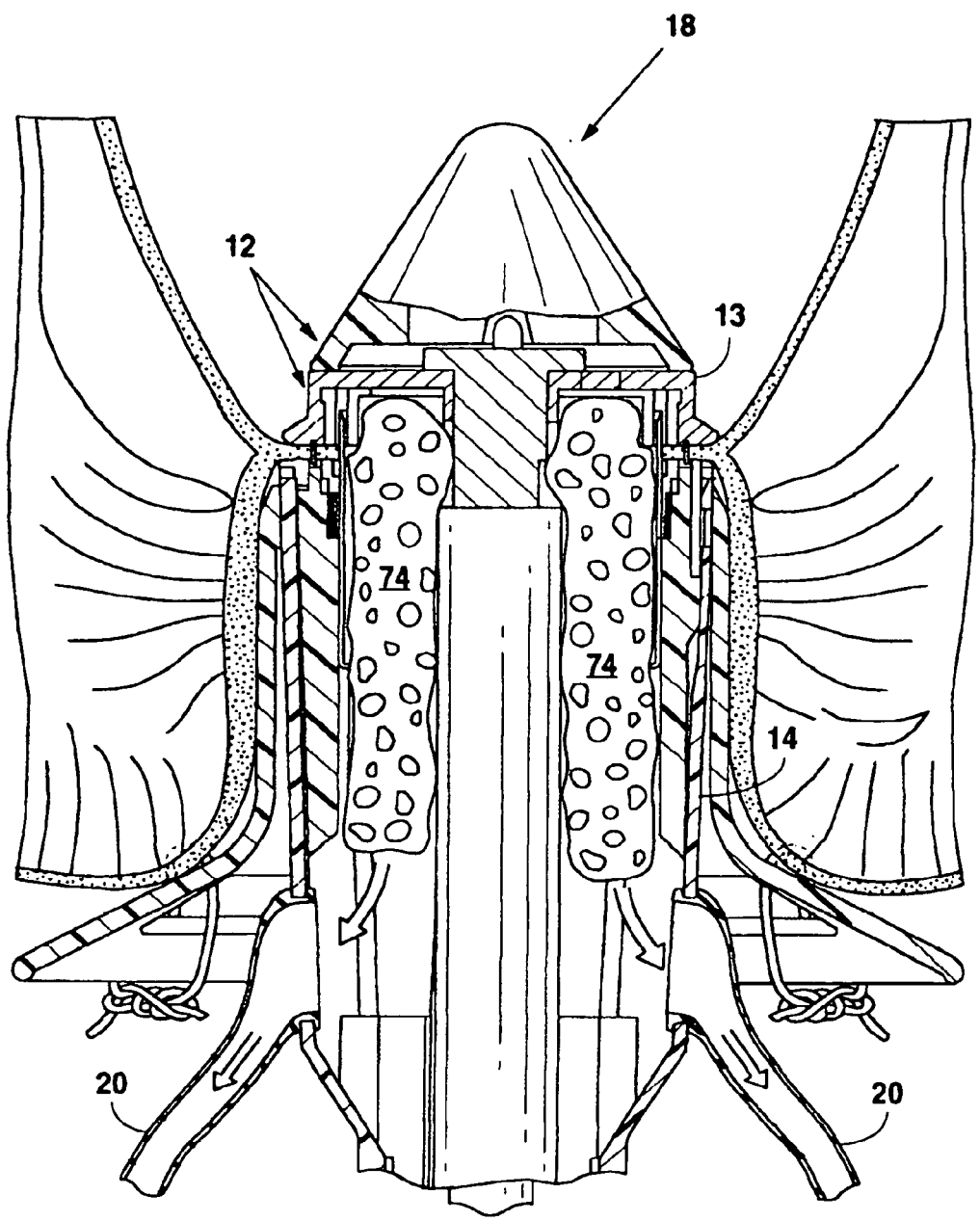
FIG. 5 is a cross-sectional view similar to FIG. 4, where the stapler has been fired to place staplers in the submucosul layer and to transect the hemorrhoidal tissue.

The head assembly 12 is capable of receiving a large amount of tissue as shown in FIGS. 3-5. Guide marks 22 on the outer housing 14 enable the user to measure the depth of anal insertion of the instrument. The anvil assembly 18 is attached to a distal end of reciprocating drive shaft 19 at the anvil shaft 24.

The stapler 10 has a handle 26 and an anvil closure knob 28. Knob 28 enables the user to move the anvil assembly proximally or distally. A firing trigger 31 is movable from an open position to a closed position to form staples into the hollow body organ and to activate the blade 62 to transect the tissue to be removed.

Figure 2:
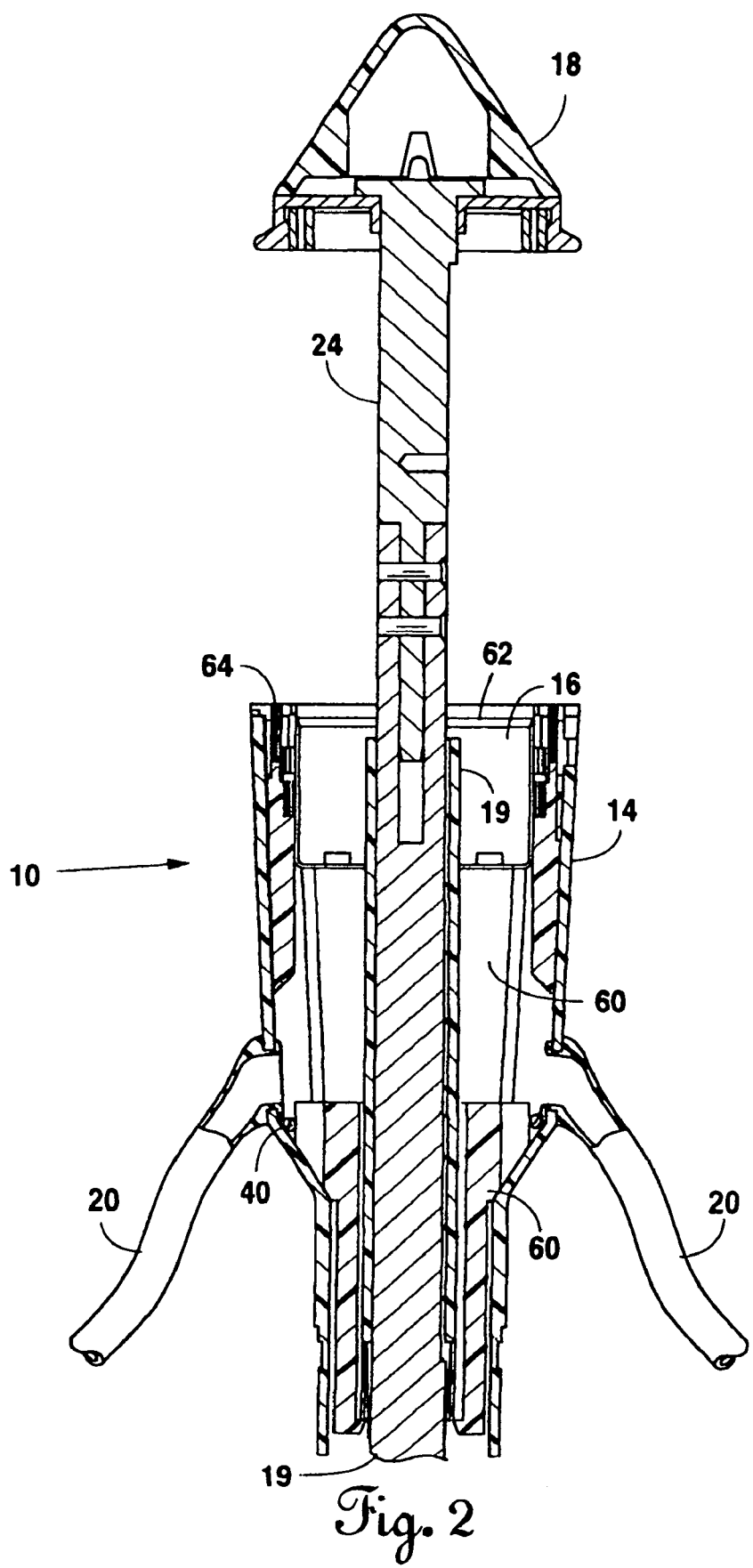
FIG. 2 is a cross-section, side elevational view of the stapler of the present invention shown in the open position.

A cross-sectional view of the present stapler 10 is shown in FIG. 2 with the vacuum tube 20 attached to the housing 14 and in communication with the inner chamber 16. Seals 40 may be provided to confine the evacuation to the upper portion of the housing, but it should be understood that a negative pressure could be drawn through the entire stapler 10 via the handle 26 and housing 14 if an alternative vacuum tube 20' (FIG. 1 broken lines) is installed at the handle end of the stapler 10.

FIG. 2 shows a stapler driver 60 received in the housing 14, a annular cutting blade 62 mounted within the distal end of the stapler driver 60, and a plurality of staples 64. As the stapler 10 is fired, the driver 60 moves from a first position (shown in FIGS. 2, 3 and 4) to a second position (FIG. 5) whereby the cutting blade 62 transects the organ and the staples 64 close the cut.

FIG. 3-5 illustrates the method of the present invention showing the stapler 10 inserted into the anus 70 and rectum 72 of the patient. The stapler head assembly 12 is positioned such that the internal hemorrhoids 74 are located between the anvil 18 and the top edge 13 of the head housing 14 with the anvil 18 in the open position. FIG. 3 shows the anvil slightly retracted beginning to "pinch" the hemorrhoid 74. As should be understood by one of ordinary skill in the art, the stapler 10 has been inserted through an anal cannula 76 sutured to the anus 70 by a series of retaining sutures 78.

FIG. 4 shows that a vacuum or negative pressure has been drawn through the vacuum tubes 20 and the hemorrhoid 74 drawn into the inner chamber 16 of the housing 14 and the anvil 18 has been further tightened or retracted to bring it closer to the edge 13 of the housing 14. The amount of suction required to draw the hemorrhoid into the chamber is just sufficient to pull the mucosal tissue but not the rectal wall 80. Dependent upon the structural strength of the hemorrhoid and the rectal wall, the effective negative pressure may be in the approximate range of 80 psi to approximately 300 psi.

FIG. 5 illustrates the complete closure of anvil 18 upon the housing 14 pinching the tissue and the stapler 10 having been fired to drive the cutting blade 62 and to insert staples so as to transect and staple the hollow body organ. The evacuating mechanism continues to draw the removed or transected tissue into the inner chamber. The evacuation is shut off when the stapler has been fired.

The stapler should be maintained in the closed position for at least twenty seconds to promote hemostasis. The anvil is opened slightly for extraction of the instrument with the removed tissue retained in the inner chamber. Further procedures to ensure successful transection of the hollow body organ are then followed by the surgeon to complete the hemorrhoidectomy.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

The invention claimed is:

1. A method for removing a circumferential portion of a hollow body organ from a patient using a circular stapling instrument comprising the steps of:

providing said circular stapling instrument comprising:
   a stapling head assembly having an outer housing with an inner chamber, a stapler driver received in said housing, a cutting blade mounted within said driver, and a means for generally evacuating said housing;
   an anvil assembly movable from an open position spaced from said housing to a closed position adjacent to said housing;

inserting said head assembly and said anvil assembly into said hollow body organ with said anvil assembly in said open position;

positioning said head and anvil within said hollow organ such that a portion of the side wall of said organ is located between said head and said anvil;

activating said means for evacuating sufficiently to draw a section of said side wall portion into said space between said head and said anvil and into said inner chamber;

moving said anvil assembly from said open position spaced from said head assembly to said closed position adjacent to said head assembly so as to clamp said drawn side wall section therebetween;

firing said circular stapling instrument so as to transect and staple said hollow body organ; and deactivating said evacuating means;

removing said head and anvil assemblies from said patient so as to remove said transected drawn section of said hollow body organ from said patient.

* * * * *